United States Patent [19]

Angersbach et al.

[11] Patent Number: 4,784,999

[45] Date of Patent: Nov. 15, 1988

[54] NOVEL TREATMENT

[75] Inventors: Dieter Angersbach; Charles D. Nicholson; Joachim Göring, all of Gronau, Fed. Rep. of Germany; Brian Morgan, Betchworth; Jonathan R. S. Arch, Epsom, both of England

[73] Assignee: Beecham Wuelfing GmbH & Co. KG, Fed. Rep. of Germany

[21] Appl. No.: 96,118

[22] Filed: Sep. 11, 1987

[30] Foreign Application Priority Data

Sep. 11, 1986 [GB] United Kingdom ............... 8621869

[51] Int. Cl.$^4$ ............................................. A61U 31/52
[52] U.S. Cl. .................................................... 514/263
[58] Field of Search ......................................... 514/263

[56] References Cited

U.S. PATENT DOCUMENTS 4,225,607  9/1980  Goring et al. .................. 514/263
4,454,138  6/1984  Goring ............................ 514/263

Primary Examiner—Stanley J. Friedman
Attorney, Agent, or Firm—Jacobs & Jacobs

[57] ABSTRACT

A method for the treatment of cerebral vascular and neuronal degenerative disorders associated with learning, memory and cognitive dysfunctions including cerebral senility, multi-infarct dementia and senile dementia of the Alzheimer type and/or peripheral vascular disease and/or proliferative skin disease in mammals, such as humans, which comprises administering to the mammal in need of such treatment an effective amount of 1,3-di-n-butyl-7-(2-oxypropyl) xanthine or a pharmaceutically acceptable salt thereof.

2 Claims, No Drawings

NOVEL TREATMENT

The present invention relates to a method for the treatment of cerebrovascular disorders and/or disorders associated with cerebral senility, peripheral vascular disease and poliferative skin diseases such as psoriasis.

German Patentschrift 926788 discloses 1,3-di-n-butyl-7-(2-oxypropyl)xanthine, herein referred to as "the compound", and a process by which is can be prepared. The compound, is described in the patent as a diuretic.

It has now been discovered that the compound has a protective effect against the consequences of cerebral metabolic inhibition and improves data acquisition or retrieval following transient forebrain ischaemia. The compound is therefore useful in the treatment of cerebral vascular and neuronal degenerative disorders associated with learning, memory and cognitive dysfunctions including cerebral senility, multi-infarct dementia and senile dementia of the Alzheimer type, in mannals including humans.

It has also bee discovered that the compound is active in increasing the oxygen tension in ischaemic skeletal muscle. This property reflects an increase in the nutritional blood flow through ischaemic skeletal muscle which in turn indicates that the compound is of potential use as an agent for the treatment of peripheral vascular disease such as intermittent claudication, in mammals including humans.

It has further been discovered that the compound acts as a phosphodiesterase inhibitor and elevates cyclic AMP levels and is therefore of potential use in the treatment of proliferative skin disease in mammals including humans.

As used herein the expression 'proliferative skin diseases' means those proliferative skin diseases which are characterized by accelerated cell division in the epidermis, dermis or appendages thereto, associated with incomplete tissue differentiation. Such diseases include psoriasis, atopic dermatitis, non-specific dermatitis, primary irritant contact dermatitis, allergic contact dermatitis, basal and squamous scaliness of the skin, lamellar ichthyosis, epidermolytic hyperkeratosis, sun induced keratosis, non-malignant keratosis, acne, and seborrheic dermatitis in humans and atopic dermatitis and mange in domesticated animals.

Accordingly, the present invention provides a method for the treatment of cerebral vascular and neuronal degenerative disorders associated with learning, memory and cognitive dysfunctions including cerebral senility, multi-infarct dementia and senile dementia of the Alzheimer type and/or peripheral vascular disease and/or proliferative skin disease in mammals, such as humans, which comprises administering to the mammal in need of such treatment an effective amount of 1,3-di-n-butyl-7-(2-oxypropyl) xanthine or a pharmaceutically acceptable salt thereof.

The administration to the mammal may be by way of oral, sub-lingual, topical or parenteral administration as appropriate.

An amount effective to treat the disorders hereinbefore described depends on the usual factors such as the nature and severity of the disorders being treated and the weight of the mammal However, a unit dose will normally contain 0.1 to 500 mg, for example 2 to 50 mg, of the compound of the invention. Unit doses will normally be administered once or more than once a day, for example 2, 3, 4, 5 or 6 times a day, more usually 2 to 4 times a day, such that the total daily dose is normally in the range, for a 70 kg adult of 0.1 to 500 mg, for example 50 to 250 mg, that is in the range of approximately 0.002 to 5 mg/kg/day, more usually 1 to 4 mg/kg/day, for example 0.7 to 2 mg/kg/day. Within this dosage range, no adverse toxicological effects are indicated with the compound It is greatly preferred that the compound is administered in the form of a unit-dose composition, such as a unit dose oral, sub-lingual or parenteral composition Such compositions are prepared by admixture and are suitably adapted for oral, sub-lingual or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use Tablets and capsules for oral and sub-lingual administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

In addition such compositions may contain further active agents such as anti-hypertensive agents and diuretics The compound may also be administered as a topical formulation, in particular for the treatment of proliferative skin disease, in combination with conventional topical excipients.

Topical formulations may be presented as, for instance, ointments, creams or lotions, impregnated dressings gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray, or aerosol formulations that may be used for the compound are conventional formulations well known in the art, for example, as described in standard text books of pharmaceutics and cosmetics, such as Harry's Cosmeticology published by Leonard Hill Books, Remington's Pharmaceutical Sciences, and the British and US Pharmacopoeias.

Suitably, the compound will comprise from about 0.5 to 20% by weight of the formulation, favourably from about 1 to 10% for example 2 to 5%.

As is common practice, the compositions will usually be accompanied by written or printed directions for use in the medical treatment concerned.

As used herein the terms "pharmaceutical composition" and "pharmaceutically acceptable" embrace compositions and ingredients for both human and veterinary use Examples of pharmaceutically acceptable salts of the compound include the hydrochloride and hydrobromide.

The present invention also provides 1,3-di-n-butyl-7(2-oxypropyl)xanthine or a pharmaceutically acceptable salt thereof for use in the treatment of cerebral vascular and neuronal degenerative disorders associated with learning, memory and cognitive dysfunctions including cerebral senility, multi-infarct dementia and senile dementia of the Alzheimer type and/or peripheral vascular disease and/or proliferative skin disease.

Such treatment may be carried out as hereinbefore described.

The present invention further provides a pharmaceutical composition for use in the treatment of cerebral vascular and neuronal degenerative disorders associated with learning, memory and cognitive dysfunctions including cerebral senility, multi-infarct dementia and senile dementia of the Alzheimer type and/or peripheral vascular disease and/or proliferative skin disease, which comprises an effective amount of 1,3-di-n-butyl-7-(2-oxypropyl) xanthine or a pharmaceutically acceptable salt thereof and a pharmaceutically acceptable carrier.

Such composition may be prepared in a manner as described hereinbefore.

In a further aspect the invention provides the use of 1,3-di-n-butyl-7-(2-oxypropyl)xanthine or a pharmaceutically acceptable salt thereof for the manufacture of a medicament for the treatment of cerebral vascular and neuronal degenerative disorders associated with learning, memory and cognitive dysfunctions including cerebral senility, multi-infarct dimentia and senile dementia of the Alzheimer type and/or peripheral vascular disease and/or proliferative skin disease.

Such composition (medicament) may be prepared in the manner as hereinbefore described.

The following pharmacological data illustrate the activity of the compound in tests which are indicative of compounds of potential use in the treatment of cerebral vascular and neuronal degenerative disorders associated with learning, memory and cognitive dysfuntions including cerebral senility, multi-infarct dementia and senile dementia of the Alzheimer type in mammals (tests 1 and 2), in peripheral vascular disease (test 3) and in proliferative skin disease such as psoriasis (test 4).

Pharmacological Data

1. Triethyltin-induced cerebral oedema in the rat

The cerebral oedema is induced by oral administrations repeated for 5 consecutive days—one administration per day—of triethyltin chloride at a dose of 2 mg/kg. The test compound is also administered orally twice daily as aqueous solution or suspension at a dose of 1 ml/100 g body-weight; these administrations are given during the 5 days of intoxication with tin. Three groups of 10 male specific pathogen-free (SPF) Wistar rats of 280±10 g body-weight are used:

1 control group
1 group intoxicated with triethyltin
1 group intoxicated with triethyltin and treated with the studied compound The rats are killed on the evening of the fifth day; the brain is removed, weighed fresh and after desiccation to constant weight and the water content of each brain is calculated [$H_2O$]=fresh weight−dry weight.

The following are then calculated
the mean water content (M+Sm %) of each group;
the protection index P due to the administered compound:

$$P\% = \left(1 - \frac{[H_2O] \text{ treated group} - [H_2O] \text{ control group}}{[H_2O] \text{ triethyltin group} - [H_2O] \text{ control group}}\right) \times 100$$

At a dose of 2×50 mg/kg, 1,3-di-n-butyl-7-(2-oxypropyl)xanthine gave a protection index P of 65% with a significance of $p<0.05$ (student's t-test).

2. The Gerbil Ischaemic Deficit Passive Avoidance Test

Mongolian gerbils were conditioned to avoid entering a dark compartment by means of a footshock (maximally 50 V, 2 s duration) received when entering from the light section of a two compartment box. Recollection of the footshock was examined 24 h later by replacing the gerbils in the two compartment box and measuring the recall latency, the time taken to re-ente the dark compartment.

Effect of test compound on recall latency in the gerbil following transient forebrain ischaemia

(a) Animal Preparation

A learning or memory deficit was induced in the gerbils by a transient (5 min) bilateral carotid artery ligation, performed 24 h prior to conditioning, under light hexobarbital anaesthesia.

(b) Measurement

Compounds, being examined for an effect on learning or memory in gerbils which had undergone carotid occlusion, were administered seven times during the experiment. The initial administration was during the period of forebrain ischaemia, the third and seventh administrations were 10 min prior to conditioning and recall testing, respectively, and the remainder were given at intermediate time points.

Results were expressed as percentage of animals which had a long recall latency (>60 s). A long recall latency indicates good information acquisition or retrieval.

(c) Results

The results for the test compound 1,3-di-n-butyl-7-(2-oxypropyl)xanthine are shown in Table 1.

TABLE I

|   |   | Percentage of animals with recall latencies >60s |
|---|---|---|
| I | sham-ligated controls | 33 |
| II | Ischaemic controls | 14** |
| III | Ischaemia and Test Compound (10 mg/kg p.o) | 36* |

*significantly different from II ($p < 0.05$).
**significantly different from I ($p < 0.05$).

As can be seen in Table 1, transient cerebral ischaemia impairs the recollection of the footstock in gerbils. The test compound significantly increased the percentage of animals with long recall latencies.

The above results show that the test compound improves data acquisition or retrieval in the gerbil following transient forebrain ischaemia and demonstrate that the compound of the invention is of potential use in the treatment of cerebral vascular and neuronal degenerative disorders associated with learning, memory and cognitive dysfunctions including cerebral senility, multi-infarct dementia and senile dementia of the Alzheimer type.

3. The effect of 1,3-di-n-butyl-7-(2-oxypropyl) xanthine on the oxygen tension ($pO_2$) of rat ischaemic gastrocnemius muscle

(a) Animal preparation

Male rats (325 to 390g), in which one femoral artery had been ligated 2-4 days previously, were anaesthetized by i.p. injection of sodium-thiopentone (100 mg/kg).

(b) Measurement

The $pO_2$ of the gastrocnemius muscle of the ischaemic hindlimb was measured with surface electrodes. An incision was made through the skin on the inside of the ischaemic limb. The thick fascia covering the muscle surface was removed carefully and the surface electrode was placed on the gastrocnemius muscle.

The electrode current was measured every 6 to 8 s and collected for periods of 4 min (Hewlett-Packard programmable data logger system 3051A). After each period, mean value and standard deviation was calculated. Muscle temperature was controlled by means of a thermocouple (Ellab, Copenhagen).

Upon a stable $pO_2$ measurement being obtained, test compound was administered intraduodenally via a plastic catheter.

The change in the muscle $pO_2$, produced by test compound administration, was calculated for each animal.

At a dose of 0.5mg/kg administered intravenously, the compound 1,3-di-n-butyl-7-(2-oxypropyl)xanthine produced a significant ($p<0.01$)* mean ($\pm$SEM; n=12) increase in $pO_2$ of $5.7\pm2.1$ torr.

*Determined using the signed rank test.

4 The inhibitory activity of 1,3-di-n-butyl-7-(2-oxypropyl)xanthine on cAMP phosphodiesterase of rat brain The activity of cyclic AMP phosphodiesterase in homogenates of rat brain was measured in the presence of various concentrations of the compound 1,3-di-n-butyl-7-(2-oxypropyl)xanthine using 0.31 $\mu$M cyclic AMP as substration. The reciprocal of the reaction rate was plotted on the y axis against each concentration of the compound on the x axis (Dixon plot). The apparent Ki value was estimated by extrapolating the steeper linear portion of the Dixon plot to the x axis and obtaining the negative intercept on the x axis. 1,3-Di-n-butyl-7-(2-oxypropyl)xanthine had an apparent Ki of 64$\mu$M.

We claim:

1. A method for the treatment of cerebral vascular and neuronal degenerative disorders related to learning, memory and cognitive dysfunctions in mammals including humans, which comprises administering to the mammal in need of such treatment an effective amount of 1,3-di-n-butyl-7-(2-oxypropyl) xanthine or a pharmaceutically acceptable salt thereof.

2. A method in accordance with claim 1 wherein the disorders treated are cerebral senility, multi-infarct dementia and senile dementia of the Alzheimer type.

* * * * *